US00PP28235P3

(12) United States Plant Patent
Braun

(10) Patent No.: US PP28,235 P3
(45) Date of Patent: Aug. 1, 2017

(54) APPLE TREE NAMED 'GALA 0502'

(50) Latin Name: ***Malus domestica* Borkh.**
Varietal Denomination: Gala 0502

(71) Applicant: KIKU SRL GmbH, Girlan/Eppan (IT)

(72) Inventor: Jürgen Braun, Girlan (IT)

(73) Assignee: KIKU SRL GmbH, Girlan/Eppan (IT)

( * ) Notice: Subject to any disclaimer, the term of this patent is extended or adjusted under 35 U.S.C. 154(b) by 0 days.

(21) Appl. No.: 14/999,113

(22) Filed: Mar. 30, 2016

(65) Prior Publication Data

US 2016/0338235 P1 Nov. 17, 2016

(30) Foreign Application Priority Data

May 15, 2015 (IT) ..... PBR BZ2015V0001

(51) Int. Cl.
*A01H 5/08* (2006.01)

(52) U.S. Cl.
USPC ..... Plt./162

(58) Field of Classification Search
USPC ..... Plt./162
See application file for complete search history.

*Primary Examiner* — Annette Para
(74) *Attorney, Agent, or Firm* — Michelle Bos Legal LLC

(57) ABSTRACT

'Gala 0502' apple is 'Gala' sport notable for its fruit, which is fully colored well before harvest, and has a distinctive solid purple-red overcolor. 'Gala 0502' can be harvested in a single picking.

6 Drawing Sheets

Latin name: *Malus domestica* Borkh.
Variety denomination: 'Gala 0502'.

BACKGROUND OF THE VARIETY

'Gala 0502' is a new and distinct variety of apple tree (*Malus domestica* Borkh), which variety originated as a limb sport mutation of 'Gala' (U.S. Plant Pat. No. 3,637, expired). 'Gala 0502' was discovered by the inventor in a cultivated orchard at Sindacale, Venezia, Italy in 2009, and was selected for further observation because of the distinctive early and even coloring of its fruit. 'Gala 0502' was first asexually propagated by chip budding in 2010 at Presina, Italy, and has since been observed to remain true to type over successive asexually propagated generations.

BRIEF DESCRIPTION OF THE VARIETY

'Gala 0502' was first selected for its fruit, which is fully colored well before harvest, and has a distinctive solid purple-red overcolor. A comparison of 'Gala 0502' to 'Gala Schnico' (U.S. Plant patent application Ser. No. 14/120,597, currently pending), 'Galaval' (U.S. Plant Pat. No. 19,909), and parent 'Gala' is set forth in Table 1 below.

TABLE 1

| Variety | Color Characteristics |
|---|---|
| 'Gala 0502' | Early homogeneous coloring, solid purple red, no stripes |
| 'Gala Schnico' | Late non-homogeneous coloring, red solid flush with some stripes |
| 'Galaval' | Red solid flush with few stripes on backside of fruit |
| 'Gala' | Bright red flush over pale yellow ground |

One hundred percent of the fruit of 'Gala 0502' can be harvested in a single pick, as compared to about fifty percent to eighty percent of 'Gala Schnico'.

BRIEF DESCRIPTION OF THE PHOTOGRAPHS

Figure 1:
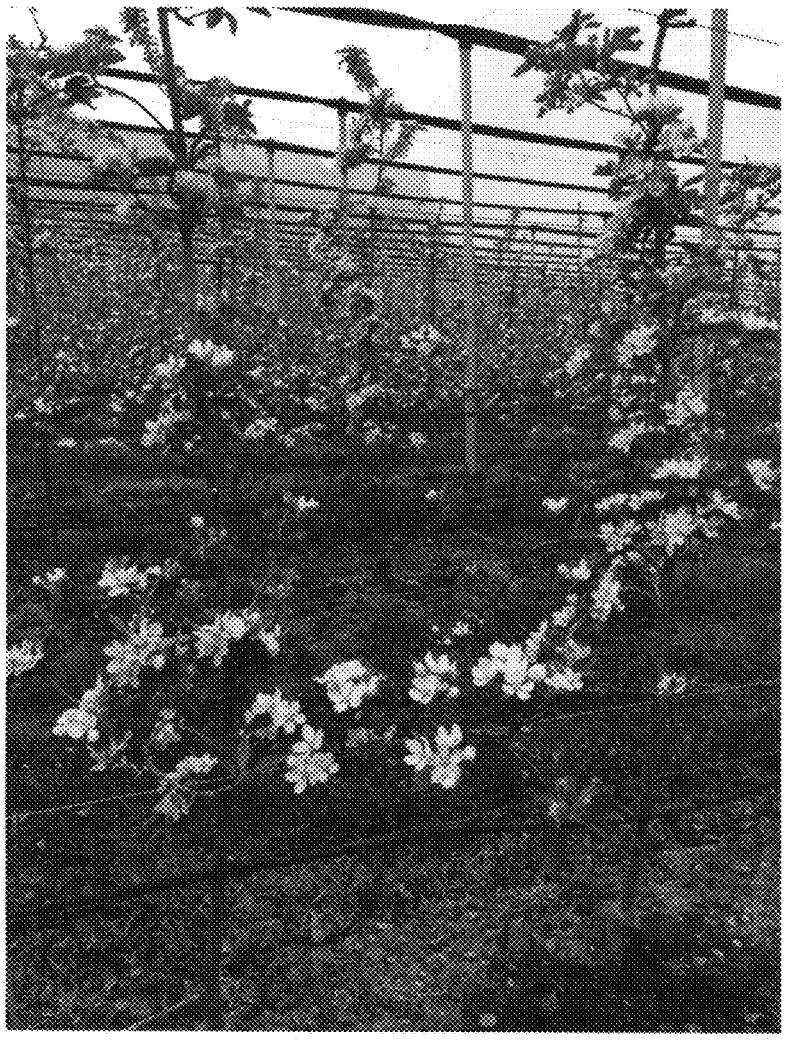
Figure 2:
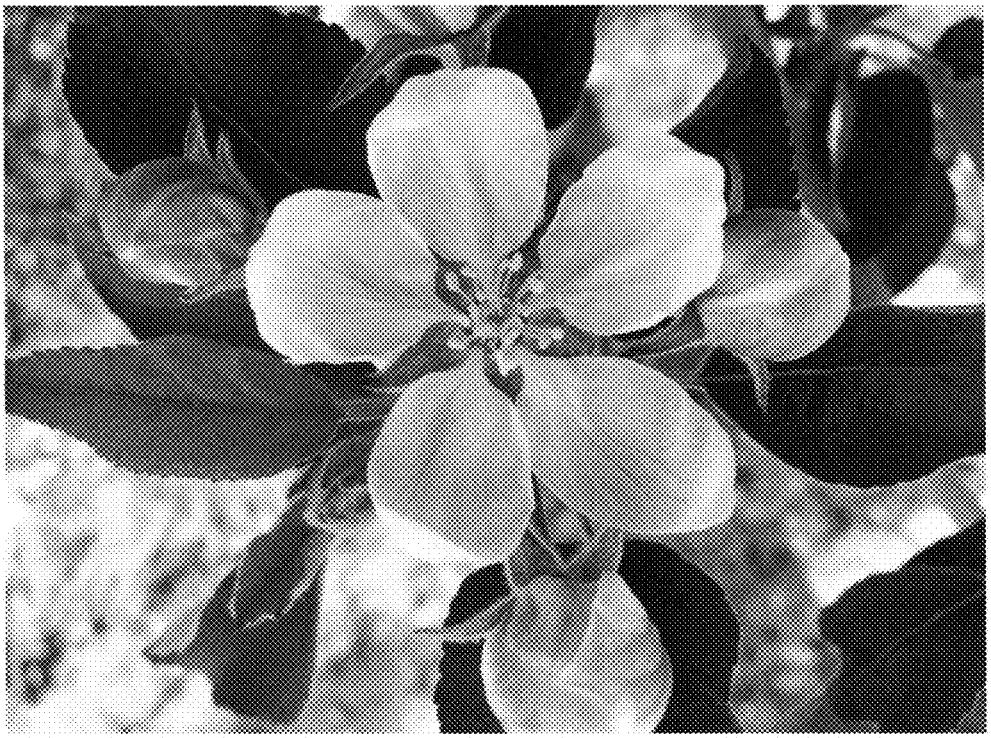
Figure 3:
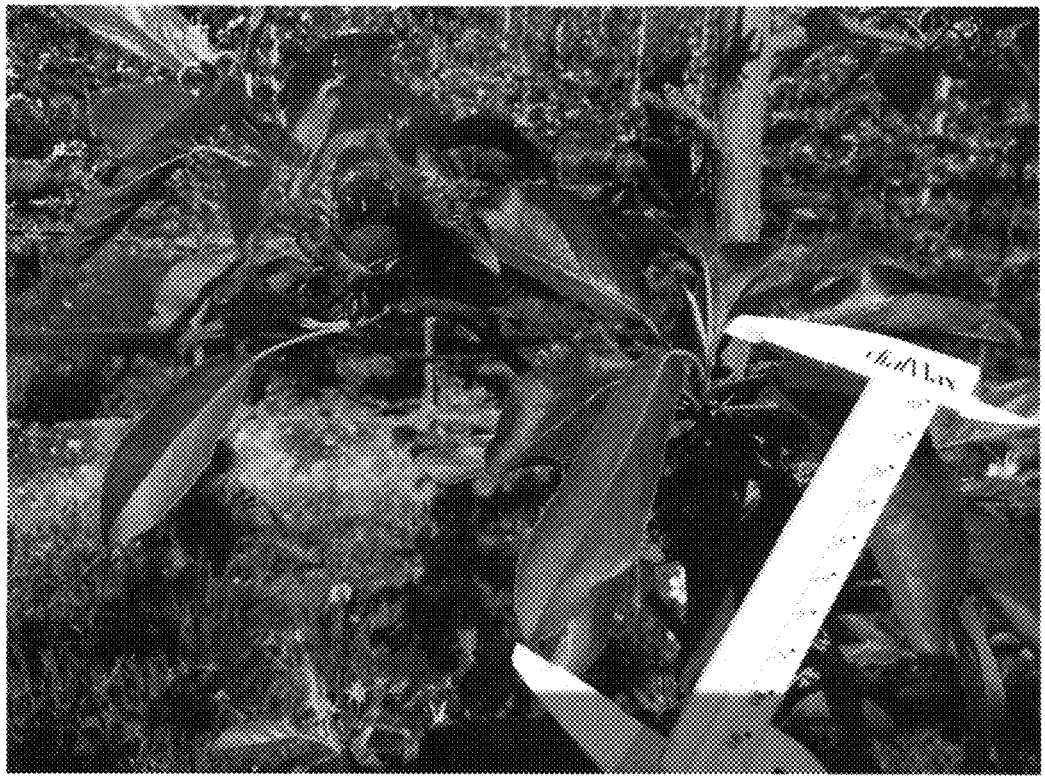
Figure 4:
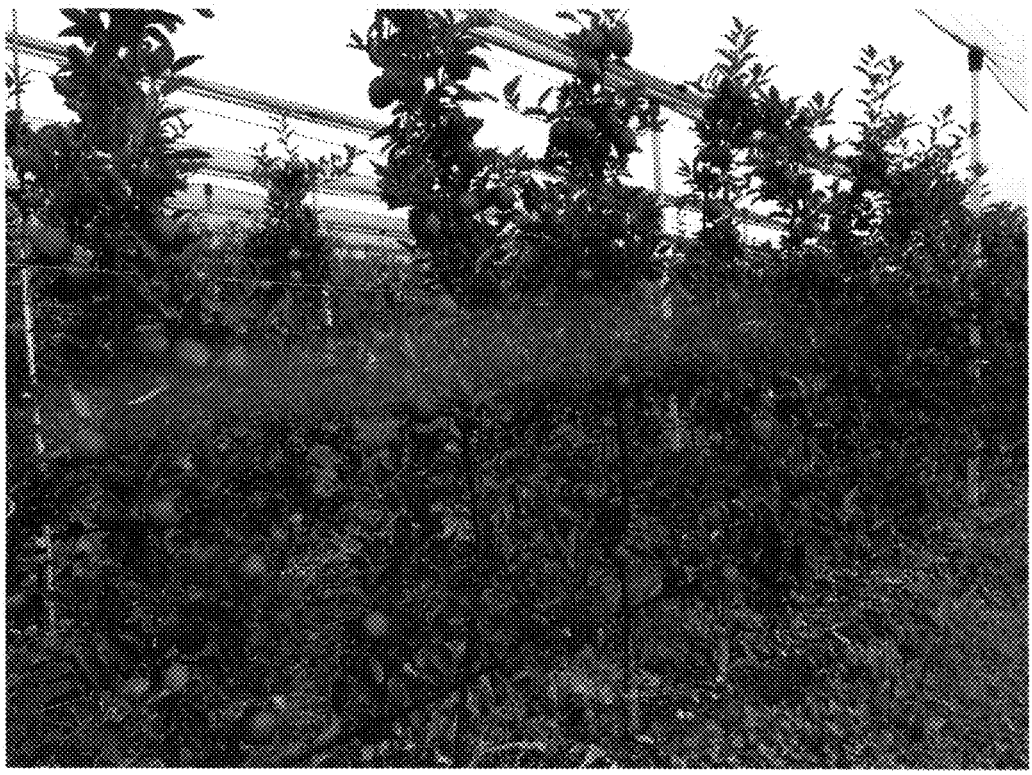
Figure 5:
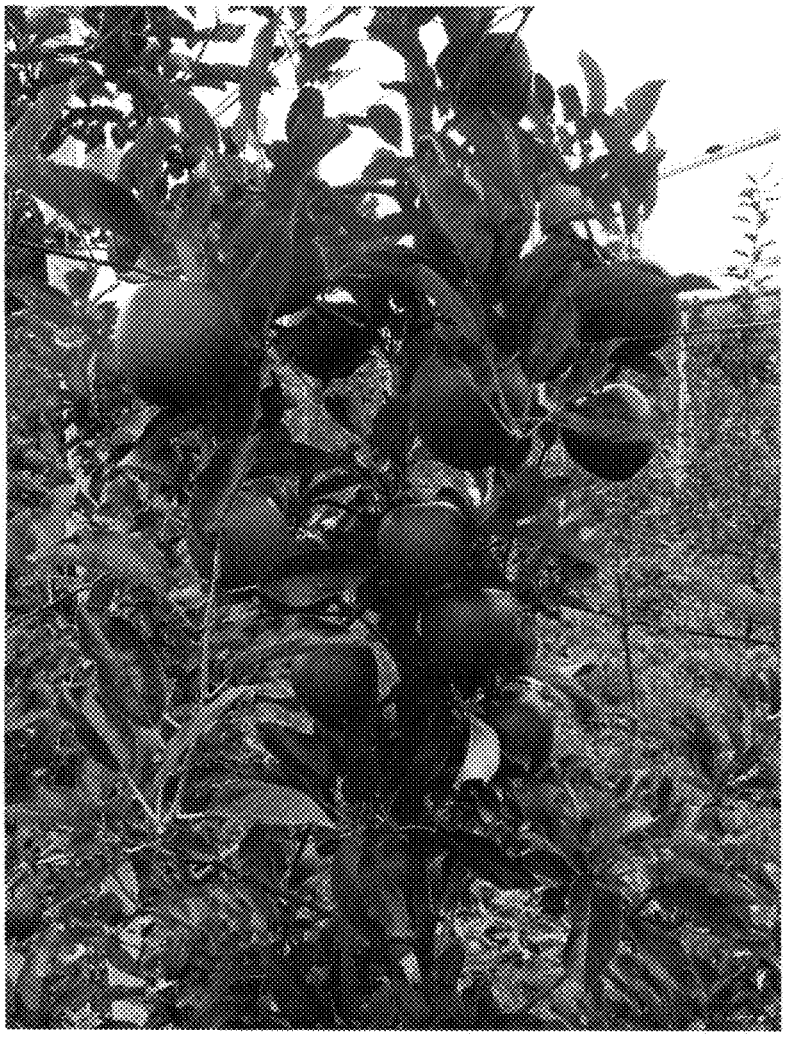
Figure 6:
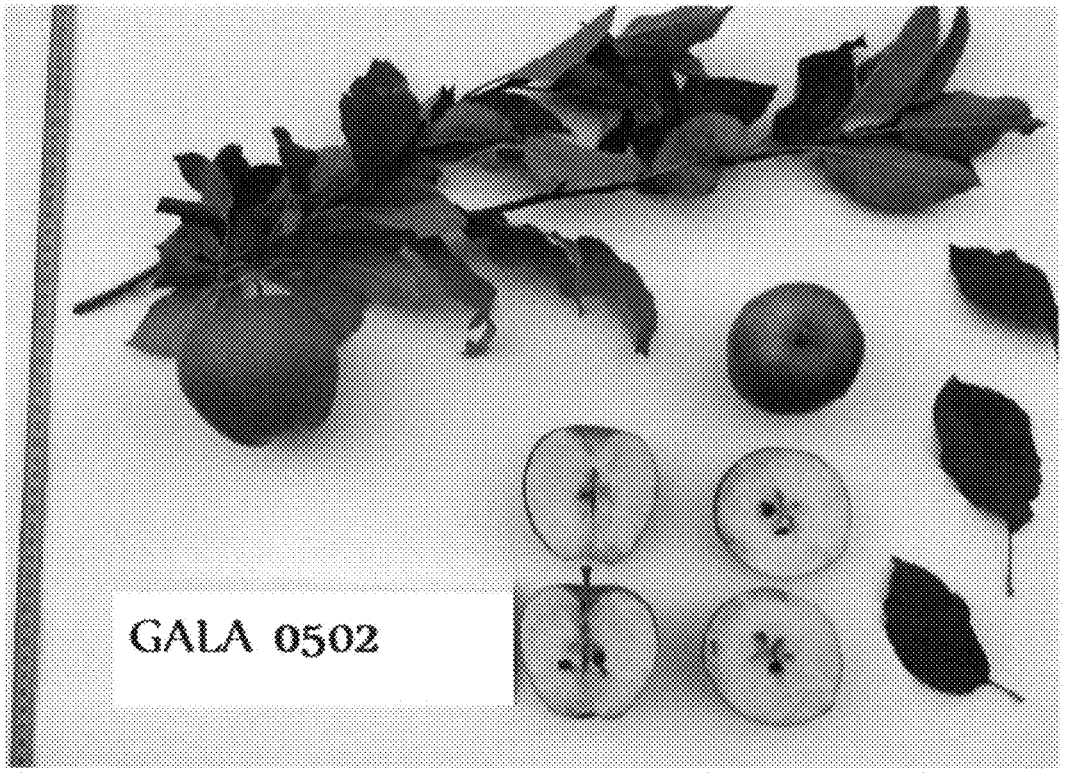

FIG. 1 shows trees of 'Gala 0502' in bloom;
FIG. 2 shows a flower of 'Gala 0502';
FIG. 3 shows the leaves and trunk of a 'Gala 0502' tree;
FIG. 4 shows trees, fruit and leaves of 'Gala 0502';
FIG. 5 shows leaves and fruit of 'Gala 0502'; and,
FIG. 6 shows leaves and whole and sectioned fruit of 'Gala 0502'.

DETAILED BOTANICAL DESCRIPTION OF THE VARIETY

The following detailed botanical description of 'Gala 0502' apple tree is based on observations made during the 2014 and 2015 growing seasons at Cornaiano, Italy of trees planted in 2012 on M9 T337 virus free rootstock. All colors are described according to The Royal Horticultural Society Colour Chart. It should be understood that the characteristics described will vary somewhat depending upon cultural practices and climatic conditions, and will vary with location and season. Quantified measurements are expressed as an average of measurements taken from a number of individual plants of the new variety. The measurements of any individual plant or any group of plants of the new variety may vary from the stated average.

Tree:

*Vigor*.—Medium (similar to other 'Gala'-type varieties).
*Type*.—Ramified.
*Habit*.—Drooping.
*Height*.—Apical dominant.
*Trunk diameter* (*at* 30 *cm above the graft*).—2.5 cm+−0.2 cm.
*Bark texture*.—Smooth.
*Bark coloration*.—Grey-brown 199A.
*Type of bearing*.—On spurs and long shoots.

Branch (fruiting branches located at around 1 m above the graft union):
- *Length.*—70 cm to 100 cm.
- *Diameter.*—1 cm+–0.1 cm at 5 cm to the stem.
- *Crotch angle.*—110 degrees+–10.
- *Bark color.*—Greyed-green 197A.
- *Lenticel length.*—0.14 cm+–0.05.
- *Lenticel color.*—Yellow-white 158A.
- *Number of lenticels per cm$^2$.*—5+–2.

One year old shoot:
- *Length.*—50 cm+–10.
- *Color.*—Grey-brown N199B.
- *Pubescence.*—Very weak.
- *Thickness.*—0.5 cm+–0.1.
- *Internode length.*—3.5 cm+–0.5.
- *Number of lenticels per cm$^2$.*—12+–2.

Flower buds:
- *Quantity per spur.*—6.
- *Shape.*—Oval.
- *Length.*—0.6 cm.
- *Diameter.*—0.4 cm.
- *Color.*—Greyed-green N187A.

Flowers:
- *Diameter of fully open flower.*—5 cm+–0.2.
- *Relative position of petal margin.*—Free.
- *Number per cluster.*—5 plus king flower.
- *Date of first bloom.*—April 10.
- *Date of full bloom.*—April 17.
- *Pollination requirement.*—'Fuji', 'Red Delicious', and 'Granny Smith' are acceptable pollenizers.

Petals: All measured on king flower.
- *Number per flower.*—5.
- *Shape.*—Oval.
- *Length.*—2.4 cm+–0.2.
- *Width.*—1.4 cm+–0.2.
- *Apex.*—Round.
- *Base.*—Pointy.
- *Margin.*—Unruffled.
- *Color of upper surface.*—White; veins red 54C.
- *Color of lower surface.*—White; veins red 54B.

Stigma:
- *Position.*—Above anthers, similar to 'Golden Delicious'.
- *Size.*—0.08 cm+–0.1.
- *Color.*—Yellow 5A.

Style:
- *Size.*—1.0 cm+–0.1.
- *Color.*—Yellow-green 145A.

Ovary:
- *Size.*—0.5 cm+–0.1.
- *Color.*—Yellow-green 144A.

Anthers:
- *Quantity.*—10+–2.
- *Size.*—0.7 cm+–0.1.
- *Presence of pollen/anther.*—Present.
- *Color of pollen/anther.*—Yellow 10A.

Pedicel:
- *Length.*—2.8 cm+–0.2.
- *Diameter.*—0.1 cm+–0.02.
- *Color.*—Yellow-green 145A.

Sepals:
- *Quantity.*—5.
- *Color.*—Green 142B.
- *Shape.*—Pointy, triangular.
- *Margin.*—Smooth.

Leaves:
- *Shape.*—Elliptic.
- *Length.*—Up to 10 cm.
- *Width.*—Up to 5 cm.
- *Length/width ratio.*—2+–0.1 to 1.
- *Blade margin.*—Serrate.
- *Apex.*—Acuminate.
- *Base shape.*—Cuneate.
- *Color of upper surface.*—Green 137A.
- *Color of lower surface.*—Green 137B.
- *Attitude in relation to shoot.*—Outward.

Petiole:
- *Length.*—4 cm+–0.1.
- *Diameter.*—1.5 cm+–0.1.
- *Color, upper surface.*—Yellow-green 152A.
- *Color, lower surface.*—Yellow-green 145A.

Fruit:
- *Quantity per cluster.*—5 maximum.
- *Diameter.*—77 mm+–7.
- *Weight.*—210 g+–30.
- *Ratio of height to width.*—1.1+–0.1 to 1.
- *General shape in profile.*—Conic.
- *Position of maximum diameter.*—Upper 50% in profile.
- *Ribbing.*—Absent or weak.
- *Crowning at calyx end.*—Moderate.
- *Size of eye.*—Small, 0.7 cm to 1 cm deep.
- *Aperture of eye.*—2.3 cm+–0.2.
- *Length of sepal.*—Long.
- *Bloom of skin.*—Medium.
- *Greasiness of skin.*—Absent.
- *Background color of skin.*—Not visible.
- *Amount of over color.*—100%.
- *Over color of skin.*—Deep red-purple 59A.
- *Intensity of over color.*—High.
- *Pattern of over color.*—Only solid flush.
- *Amount of russet around stalk cavity.*—Absent or small.
- *Amount of russet on cheeks.*—Absent.
- *Area of russet around eye basin.*—Absent.
- *Length of stalk.*—2.1 cm+–0.2.
- *Thickness of stalk.*—0.3 cm+–0.1.
- *Depth of stalk cavity.*—1.4 cm+–0.2.
- *Width of stalk cavity.*—1.6 cm+–0.2.
- *Firmness of flesh.*—Medium, 6.5 kg per cm$^2$.
- *Flesh texture.*—Crunchy.
- *Aroma.*—Sweet.
- *Juiciness.*—Very juicy.
- *Brix.*—14 to 15.
- *Flesh color.*—Yellow 10D.
- *Number of lenticels per cm$^2$.*—5+–2.
- *Size of lenticels.*—Large, up to 3 mm.
- *Aperture of locules.*—Moderately open.
- *Stem coloration.*—Greyed-orange 177A.

Seeds:
- *Quantity per fruit.*—Max 2 per chamber, max 10 total.
- *Shape.*—Teardrop.
- *Length.*—0.8 cm+–0.1.
- *Width.*—0.45 cm+–0.1.
- *Color.*—Greyed-orange 177A.

Harvest:
- *Time for harvest.*—Mid August, similar to other 'Gala'-types.
- *Number of picks.*—1.
- *Amount of fruit produced per tree per harvest.*—20 kg+–2.

Disease resistance/susceptibility: Similar to other 'Gala'-types.

Market use: Fresh market.

Storageability: Stores well from picking time up to April under proper storage conditions.

I claim:

1. A new and distinct apple tree, substantially as described and illustrated herein.

* * * * *